US009442087B2

(12) United States Patent
Bao et al.

(10) Patent No.: US 9,442,087 B2
(45) Date of Patent: Sep. 13, 2016

(54) ORGANIC THIN-FILM TRANSISTOR SENSOR ARRANGEMENTS

(71) Applicant: The Board of Trustees of the Leland Stanford Junior University, Palo Alto, CA (US)

(72) Inventors: Zhenan Bao, Stanford, CA (US); Mark E. Roberts, Albuquerque, NM (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 14/537,690

(22) Filed: Nov. 10, 2014

(65) Prior Publication Data

US 2015/0064798 A1    Mar. 5, 2015

Related U.S. Application Data

(62) Division of application No. 11/781,749, filed on Jul. 23, 2007, now abandoned.

(60) Provisional application No. 60/832,838, filed on Jul. 24, 2006.

(51) Int. Cl.
  *G01N 27/02*  (2006.01)
  *G01N 27/06*  (2006.01)
  *H01L 51/05*  (2006.01)

(52) U.S. Cl.
  CPC ............. *G01N 27/02* (2013.01); *H01L 51/052* (2013.01); *H01L 51/0558* (2013.01)

(58) Field of Classification Search
  CPC ........................................ G01N 27/06–27/129
  See application file for complete search history.

(56) References Cited

U.S. PATENT DOCUMENTS

| 6,203,981 | B1 * | 3/2001 | Ackley | G01N 33/5438 422/50 |
| 6,287,776 | B1 | 9/2001 | Hefti | |
| 7,189,987 | B2 | 3/2007 | Bao et al. | |
| 2002/0048531 | A1 * | 4/2002 | Fonash | B81C 1/0038 422/68.1 |
| 2004/0195563 | A1 * | 10/2004 | Bao | G01N 27/4145 257/40 |
| 2004/0245527 | A1 | 12/2004 | Tsukagoshi et al. | |
| 2005/0053524 | A1 | 3/2005 | Keersmaecker et al. | |

(Continued)

OTHER PUBLICATIONS

Someya et al. "Integration and Response of Organic Electronics with Aqueous Microfluidics," 18 Langmuir, 5299-5302 (2002).

(Continued)

*Primary Examiner* — Raj R Gupta
(74) *Attorney, Agent, or Firm* — Crawford Maunu PLLC

(57) ABSTRACT

A sensor includes an organic thin-film transistor (OTFT) that operates under low voltage conditions in an aqueous environment. According to an example embodiment, an OTFT includes an organic channel that electrically connects source and drain electrodes, with a gate electrode separated from the channel by a dielectric layer. The channel, gate and dielectric layer are arranged to facilitate switching of the channel region to pass current between the source and drain electrodes, in response to a low voltage applied to the gate electrode, when the channel is exposed to an aqueous solution. The current that is passed is indicative of characteristics of the aqueous solution, and is used to characterize the same. For various implementations, the low voltage operation of the sensor facilitates such characterization with substantially no ionic conduction through an analyte in the aqueous solution.

21 Claims, 3 Drawing Sheets

(56) References Cited

U.S. PATENT DOCUMENTS

2007/0152669 A1    7/2007  Park et al.
2008/0012007 A1*   1/2008  Li .................... G01N 27/4145
                                                            257/40

OTHER PUBLICATIONS

Yoon et al. "Low-Voltage Organic Field-Effect Transistors and Inverters Enabled by Ultrathin Cross-Linked Polymers as Gate Dielectrics," 127 J. Am Chem. Soc., 10388-10395 (2005).

Facchetti et al. "Gate Dielectrics for Organic Field-Effect Transistors: New Opportunities for Organic Electronics," Adv. Mater., 17, 1705-1725 (2005).

Schroeder et al. "High-Performance Organic Transistors Using Solution-Processed Nanoparticle-Filled High-k Polymer Gate Insulators," Adv. Mater., 17, 1535-1539 (2005).

Chen et al. "Organic thin-film transistors with nanocomposite dielectric gate insulator, Applied Physics Letters," col. 85, No. 15 (2004).

Bao et al. Appeal No. 2012-003864 (U.S. Appl. No. 11/781,749). PTAB Decision (Sep. 8, 2014).

* cited by examiner

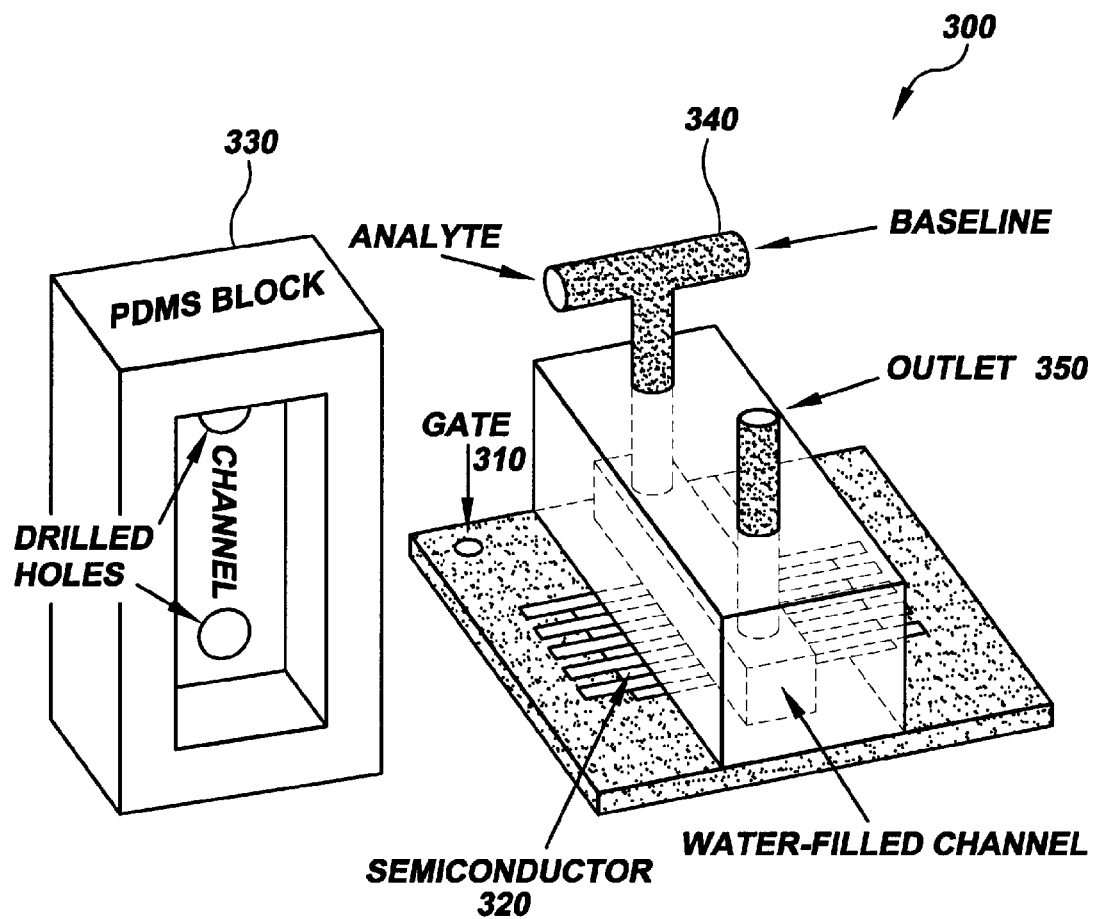

ORGANIC THIN-FILM TRANSISTOR SENSOR ARRANGEMENTS

RELATED PATENT DOCUMENTS

This patent document is a divisional under 35 U.S.C. §120 of U.S. patent application Ser. No. 11/781,749 filed on Jul. 23, 2007, which claims the benefit, under 35 U.S.C. §119(e), of U.S. Provisional Patent Application No. 60/832,838 filed Jul. 24, 2006, entitled: "Cross-Linked Organic Thin-Film Dielectrics;" each of these patent documents is fully incorporated herein by reference.

FEDERALLY-SPONSORED RESEARCH OR DEVELOPMENT

This invention was made with Government support under contract 0213618 awarded by the National Science Foundation. The U.S. Government has certain rights in this invention.

FIELD OF THE INVENTION

The present invention relates generally to semiconductor devices, and more particularly to sensor arrangements and approaches involving organic thin-film transistors.

BACKGROUND

The detection and analysis of samples has become increasingly important in a variety of fields and industries, including those relating to healthcare, environmental applications, laboratory research and national defense. For example, the detection of sample materials such as chemical or biological species is useful for identifying the samples and/or characterizing a particular solution in which the samples are present. In the healthcare industry, these approaches are useful in analyzing blood and other fluids. In environmental applications, these approaches are useful in analyzing lakes, rivers, water supplies and treatment facilities.

Approaches to sample detection have been limited for a variety of reasons. In many applications, sample detection has required expensive labeling and detection equipment. In addition, while it is often desirable to detect samples in a variety of environments, many sensors are not amenable to use with certain environments. For instance, detecting analytes has been challenging in environments susceptible to moisture. Detection has been particularly challenging under conditions involving analytes that are in solution such as an aqueous solution, as often is the case for comprehensive environmental monitoring and biological sensing.

One relatively economical and flexible device that has been used in sensing applications is the organic thin-film transistor (OTFT). OTFTs are useful for performing a variety of functions and offer unique characteristics desirable for many applications. See, e.g., Sze, S. M. *Semiconductor Devices: Physics and Technology*, 2nd edition; Wiley: New York, 1981. Generally, OTFTs are low in weight, flexible in application and inexpensive; as such, OTFTs are useful for a multitude of applications.

While OTFTs are useful for many applications, their manufacture and implementation for sensor applications has been challenging. Generally, OTFTs have not been suitable for applications involving exposure to moisture and aqueous solutions due to high operating voltages, degradation and delamination under aqueous conditions, and in particular under conditions that expose a significant portion of the OTFT to a solution. See, e.g., Someya, T., et al., *Integration and response of organic electronics with aqueous microfluidics*, Langmuir, 2002, 18(13): p. 5299-5302, incorporated herein by reference. Dielectric materials used in OTFTs have generally been susceptible to the formation of pinholes, which introduce undesirable characteristics. Many applications directed to the formation of OTFTs require relatively high temperature (e.g., over 150° C., or over 200° C.), which can present challenges to the implementation of certain materials. Other challenges to the formation of OTFTs relate to processing characteristics, including those related to the ease, consistency and quality of the manufacture of dielectric layers for OTFTs. For instance, many manufacturing approaches are characterized by undesirable moisture sensitivity, high reactivity, and rough surfaces. Still other challenges to the implementation of OTFTs are related to compatibility with different gate and channel materials, and with organic semiconductors.

These and other characteristics have been challenging to the design, manufacture and use of sensors and, in particular, of sensors used in moisture-susceptible environments.

SUMMARY OF THE INVENTION

The present invention is directed to overcoming the above-mentioned challenges and others related to the types of applications discussed above and in other applications. These and other aspects of the present invention are exemplified in a number of illustrated implementations and applications, some of which are shown in the figures and characterized in the claims section that follows.

According to an example embodiment of the present invention, an apparatus for sensing characteristics of an aqueous solution includes an organic transistor having a source, a drain, an organic semiconducting channel between the source and the drain, and a dielectric layer electrically arranged between a gate and the channel. The organic transistor responds to a low voltage at the gate for operating the apparatus in a sensing state in which current through the channel changes in response to the channel being exposed to the aqueous solution and in which the current in the channel is used to characterize the aqueous solution.

According to another example embodiment of the present invention, an organic sensor includes a substrate including a channel, a gate electrode, source and drain electrodes connected by the channel, and a dielectric layer electrically arranged between the channel and the gate electrode. The dielectric layer includes an organic polymer cross-linked with a reaction-stabilized polymer-cross-linking material.

For use in sensing characteristics of aqueous solutions, another example embodiment is directed to an organic thin-film transistor (OTFT) sensor arrangement having a plurality of OTFTs, a controller to control the OTFTs and a detector to detect a response of the OTFTs to a solution. Each OTFT includes source and drain electrodes, an organic substrate having a channel electrically arranged between the source and drain electrodes, a gate electrode over the substrate, and a dielectric layer electrically arranged between the channel and the gate electrode. The channel conducts current in response to characteristics of an aqueous solution to which it is exposed. The controller applies a low voltage to the gate electrode of each of the OTFTs to control the channel for electrically coupling the source and drain electrodes. The detector is electrically coupled to an electrode of each of the OTFTs to detect a characteristic of the aqueous solution to which the channel of each OTFT is exposed.

The above summary is not intended to describe each illustrated embodiment or every implementation of the present invention.

BRIEF DESCRIPTION OF THE DRAWINGS

The invention may be more completely understood in consideration of the detailed description of various embodiments of the invention that follows in connection with the accompanying drawings, in which:

FIG. 3 shows a sensor arrangement for detecting chemicals in aqueous solutions, according to another example embodiment of the present invention.

Figure 1:
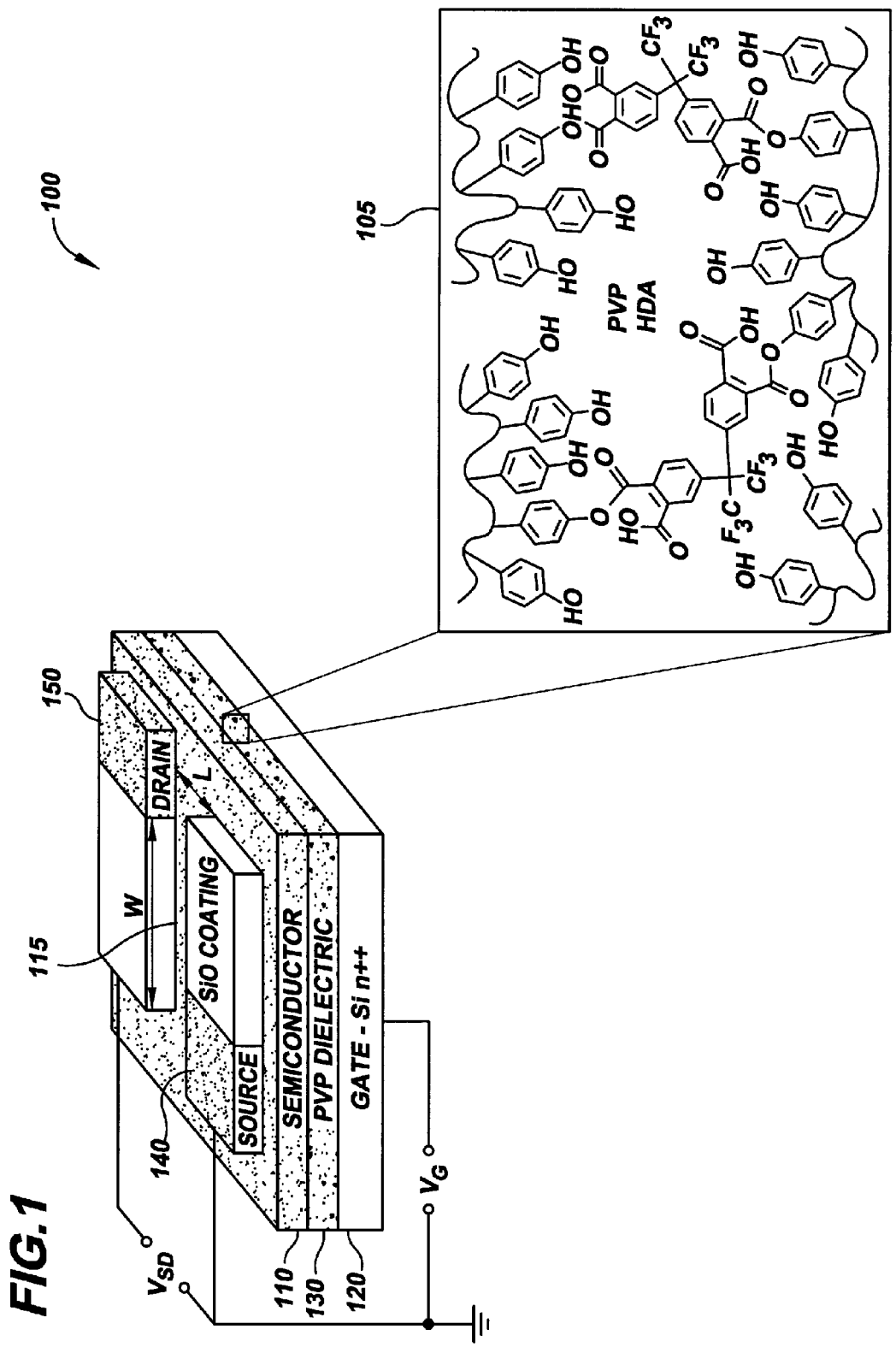
FIG. 1 shows an organic sensor device, according to an example embodiment of the present invention.

While the invention is amenable to various modifications and alternative forms, examples thereof have been shown by way of example in the drawings and will be described in detail. It should be understood, however, that the intention is not to limit the invention to the particular embodiments shown and/or described. On the contrary, the intention is to cover all modifications, equivalents, and alternatives falling within the spirit and scope of the invention.

DETAILED DESCRIPTION

The present invention is believed to be applicable to a variety of different types of sensor-based processes, devices and arrangements involving organic thin-film transistors. While the present invention is not necessarily so limited, various aspects of the invention may be appreciated through a discussion of examples using this context.

In connection with various example embodiments of the present invention, low-operating voltage organic thin-film transistor (OTFT) sensors exhibit stable operation (e.g., over a multitude of electrical cycles) under aqueous conditions. The OTFT sensors are implemented for environmental sensing, healthcare diagnosis, biological testing (e.g., national defense), chemical detection and research. In some applications, the OTFT sensors facilitate aqueous-phase sensing for samples in solution having concentrations as low as parts per billion such as trinitrobenzene, methylphosphonic acid, cysteine and glucose. In other applications, the OTFT sensors facilitate the detection of solution characteristics such as pH.

In connection with one embodiment, an organic sensor includes an OTFT having an electrode, a source and drain, an organic semiconducting channel connecting the source and drain, and a dielectric layer electrically arranged between the electrode and the channel. The channel is exposed to a solution having an analyte (or analytes), or exhibiting other characteristics to be detected. The gate electrode controls the conductivity in the channel between the source and drain in response to a low voltage applied to the electrode. This application of low voltage operates the OTFT under conditions for detecting characteristics of the solution by way of the solution's influence upon the conductivity of the channel (and thus the current flow between the source and drain) as relevant, for example, to interactions at an interface between the channel and dielectric layer. This current flow is detected and used to characterize the composition of the solution (e.g., an analyte as discussed above) or, more generally, to characterize aspects of the solution such as pH.

In connection with various embodiments, chemical sensing is made possible by the presence of grain boundaries in a semiconductor film of the OTFT sensor, which provides a pathway for the diffusion of small molecules or ions to the semiconductor-dielectric interface. These small molecules or ions influence charge transport in the active layer and, corresponding, influence current that is passed between source and drain electrodes of the OTFT. With these approaches, response time of the OTFT as related to molecule/ion size is consistent with the above mechanism (i.e., response time is faster for smaller $H^+$>Cysteine>MPA>glucose>the larger trinitrobenzene (TNB).

For certain applications, the drain current is dependent on the concentration of hydronium ions, which can effectively dope the semiconductor film. In other applications, the drain current depends upon other analyte species in solution, such as upon the conversion of an analyte binding event. With these applications, a decrease in drain current may be observed as a result of charge trapping at the dielectric interface from the polar analyte species or local screening of the electric field. As is relative to these examples, for inorganic nanowire sensors, protons assemble at the surface of the oxide and counter the gate field rather than diffusing into the active layer, which can lead to an opposite change in current.

In the context of the various example embodiments described herein, the term (and terms relating to) low operating voltage generally refer to an operating voltage that facilitates sample detection without causing undesirable conditions such as those relating to ionic conduction (via a sample analyte) or electrolytic hydrolysis of water in the solution. In this context, the terms "without causing" relate to causing substantially low (e.g., almost no) ionic conduction or electrolytic hydrolysis and as such relate to none of these, or substantially none. For instance, such applications involve sample detection wherein conductivity in the channel is generally or relatively unaffected, such as when the semiconductor channel current is orders of magnitude greater than the current through the analyte. In some applications, such a voltage is less than about 5 V, in other applications, less than about 1-2 V and in still other applications, less than about 500 mV. The dielectric and gate of OTFTs used in these contexts facilitate such operation by applying an electric field in response to voltage application that is sufficient to couple source and drain electrodes of the OTFT for detecting a sample in the solution, without bringing about the above-discussed undesirable conditions. While example dielectric materials (e.g., cross-linked poly(4-vinylphenol) (PVP)) and semiconductor materials (e.g., pentacene, carbon nanotubes) are described, other materials that facilitate the above characteristics relative to low-voltage operation (i.e., as relative to dielectric capacitance and thickness) are used in connection with various embodiments.

Also in the context of various examples, exposure of OTFT devices to aqueous solutions involves exposing some or all of a channel of the OTFT, and in some applications, exposure of one or both of source and drain electrodes. In these contexts, certain applications involve the introduction of a flow of aqueous solution (e.g., as described in connection with FIG. 3), other applications involve exposure of an entire semiconductor layer including the channel to a back-gated OTFT sensor, and other applications involve immersion of OTFT sensors in a solution.

Turning now to the Figures, FIG. 1 shows an organic sensor device 100 according to another example embodiment of the present invention. The device 100 includes a semiconductor layer 110 separated from a back gate 120 by a dielectric layer 130. Source and drain regions 140 and 150 are formed on the semiconductor layer 110, which includes a channel 115 between the source and drain regions.

The dielectric layer 130 includes a dielectric material suitable for compatibility with the semiconductor layer 110 and for operating the channel 115 under conditions that facilitate conduction between the source and drain 140 and 150 in response to a low voltage applied at the gate 120. When switched on by an electric field applied at the gate 120 via the dielectric layer 130 and exposed to a solution, the channel 115 conducts electricity between the source 140 and drain 150 in a manner that is responsive to characteristics of the solution.

In one implementation and as represented in the inset 105, the polymer matrix for the dielectric layer 130 is poly(4-vinylphenol) (PVP), which exhibits desirable dielectric characteristics and compatibility with various organic semiconductors. PVP's hydroxyl groups are suitable functional groups for cross-linking with a variety of commercially available, ambient-stable cross-linkers such as 4,4'-(hexafluoroisopropylidene)diphthalic anhydride (HDA, as shown in the inset 105) and suberoyl chloride (SC) (in other embodiments).

The dielectric layer 130 is formed in one or more of a variety of manners; the following describes example approaches. A catalytic amount of triethylamine is used to promote a PVP cross-linking reaction with HDA, and ultrathin films of the PVP-HDA solution are spin-coated onto the gate 120. The spin-coated solution is cured at a temperature that facilitates cross-linking (e.g., about 90° C.). In some applications, the film is formed to a thickness of about 10 nm and exhibits a capacitance of up to about 406 nF/cm$^2$, and in other applications, the film is formed to a thickness of about 22 nm and exhibits a capacitance of about 166 nF/cm$^2$ and a corresponding dielectric constant of about 4.2. With these approaches, the PVP-HDA dielectric layer 130 exhibits relatively low leakage currents, (e.g., less than about $10^{-6}$ A/cm$^2$ for 22 nm, and less than $10^{-8}$ A/cm$^2$ for 56 nm, at an applied voltage of below about 2 V).

For general information regarding dielectrics, and for specific information regarding other dielectric materials that may be used in connection with dielectric layer 130 and other example embodiments involving OTFT sensors as described herein, reference may be made to the following publications, each of which is incorporated herein by reference: Chua, L. L., et al., *High-stability ultrathin spin-on benzocyclobutene gate dielectric for polymer field-effect transistors*, Applied Physics Letters, 2004. 84(17): p. 3400-3402; Chua, L. L., et al., *General observation of n-type field-effect behaviour in organic semiconductors*, Nature, 2005, 434(7030): p. 194-199; Yoon, M. H., et al., *Low-voltage organic field-effect transistors and inverters enabled by ultrathin cross-linked polymers as gate dielectrics*, Journal of the American Chemical Society, 2005. 127(29): p. 10388-10395; and Facchetti A.; Yoon M. H. and Marks T. J.; *Gate dielectrics for organic field-effect transistors: New opportunities for organic electronics*, Advanced Materials 17 (14): 1705-1725 Jul. 18, 2005.

The semiconductor layer 110 includes one or more of a variety of organic materials amenable to use with sensor applications as described herein. In some embodiments, the semiconductor layer 110 includes p-channel semiconductors such as pentacene, 5,5'-bis-(7-dodecyl-9H-fluoren-2-yl)-2,2'-bithiophene (DDFTTF) and copper(II) phthalocyanine. In other embodiments, the semiconductor layer 110 includes an n-channel semiconductor such as copper(II) 1,2,3,4,8,9,10,11,15,16,17,18,22,23,24,25-hexadecafluoro-29H,31H-phthalocyanine (FCuPc). These semiconductors may be thermally evaporated onto PVP-HDA (22 nm) coated substrates. Other applications involve the use of a carbon nanotube as the channel 115, integrated with and/or separately from the semiconductor layer 110 as shown. The following three examples describe implementations of the semiconductor layer 110.

Using pentacene as the semiconductor layer 110 at a thickness of about 40 nm, the OTFT device 100 exhibits a mobility of about 1.5 cm$^2$/Vs and an on/off ratio of about $5 \times 10^4$ with a bias of about 1 V applied to the gate 120. In some applications, the dielectric layer 130 is treated with octadecyltriethoxysilane (OTS) to reduce leakage current, facilitating a relatively high mobility and an on/off ratio (e.g., as high as 3 cm$^2$/Vs and an on/off ratio of $10^6$ at gate bias of 2 V).

Using DDFTTF as the semiconductor layer 110 at a thickness of about 40 nm, the OTFT device 100 exhibits desirable current response characteristics and in some applications, exhibits a mobility as high as about 0.39 cm$^2$/Vs (0.2 cm$^2$/Vs average) and an on/off ratio of $2 \times 10^5$ at a gate bias of about 2 V.

Using air stable n-channel FCuPc as the semiconductor layer 110 under operating voltages of 1-2 V, the OTFT device 100 exhibits a mobility of about 0.045 cm$^2$/Vs and an on/off ratio of greater than about $10^3$.

The source 140 and drain 150 electrodes are formed on the semiconductor layer 110 using, for example, gold deposited to form a channel width (W, as shown) of about 1 mm and a channel length (L, as shown) of about 50 μm.

In some example embodiments, the dielectric layer 130 is formed using an organic polymer such as a hydroxyl-including or phenol-including polymer (e.g., polyvinyl alcohol or polyvinylphenol (PVP)) in a cross-linking solution that is reaction-stabilized and amenable to low-temperature cross-linking. The solution includes an organic polymer material and a reaction-stabilized cross-linking material that links the organic polymer material together upon reaction. In this context, the reaction-stabilized polymer-cross-linking material is a material that is stable with the organic polymer such that a solution containing both the cross-linking and polymer materials is reaction-stabilized (e.g., exhibits a low rate of reaction) over an extended time period. That is, the cross-linking material can be maintained in solution with the polymer material for an extended time before applying the solution to form the dielectric layer by reacting the materials to cross-link the polymer. For instance, such a cross-linking material involves, in some applications, a cross-linking material that is stable in that it does not form a polymer with itself. Furthermore, the reaction-stabilized cross-linking material is a material that cross-links with the polymer at an elevated temperature (e.g., greater than room temperature) that is less than about 140° C.

In some applications, a time-stabilized (polymer and cross-linking) solution as discussed above exhibits a polymer/cross-linking rate of reaction that is generally low, facilitating stability of the polymer and cross-linking solution for several hours, days or even weeks. For instance, one type of polymer and cross-linking solution has a rate of reaction such that less than about 10% of an —OH group on the polymer is cross-linked over a time period of one or two days, and in some instances, several days (e.g., about 6 days). In certain applications, a polymer and cross-linking solution exhibits less than about 5% reaction of an —OH group over similar time periods. In other applications, the reaction rate and corresponding time periods are related to the ratio of the polymer to cross-linking material.

For certain applications, the reaction-stabilized polymer-cross-linking material is reaction-stabilized with water. In such applications, the reaction-stabilized polymer-cross-linking material is amenable to use in conditions susceptible to water or humidity, such as with an in-solution condition, where the polymer-cross-linking material is exposed to water prior to its use in the formation of a dielectric layer. In some applications, the polymer-cross-linking material is stable in-solution with water, such that less than about 20% of the material reacts with water over a period of about 1 hour, and in other applications, less than about 5% of the cross-linking material reacts with water in about an hour.

According to another example embodiment of the present invention, the dielectric layer 130 includes a PVP polymer with one or more of a variety of reaction-stabilized cross-linking agents. In some applications, the cross-linking occurs through the formation of an ester bond between a hydroxyl group of a PVP monomer and a reactive group of a small molecule containing at least two reactive groups, such as an acyl chloride, anhydride, carboxylic acid or isocyanate. In some reactions using an anhydride or carboxylic acid, a reaction promoting agent such as a catalytic amount of an organic base is included in a reaction mixture with the PVP monomer and the reactive group.

Figure 2:
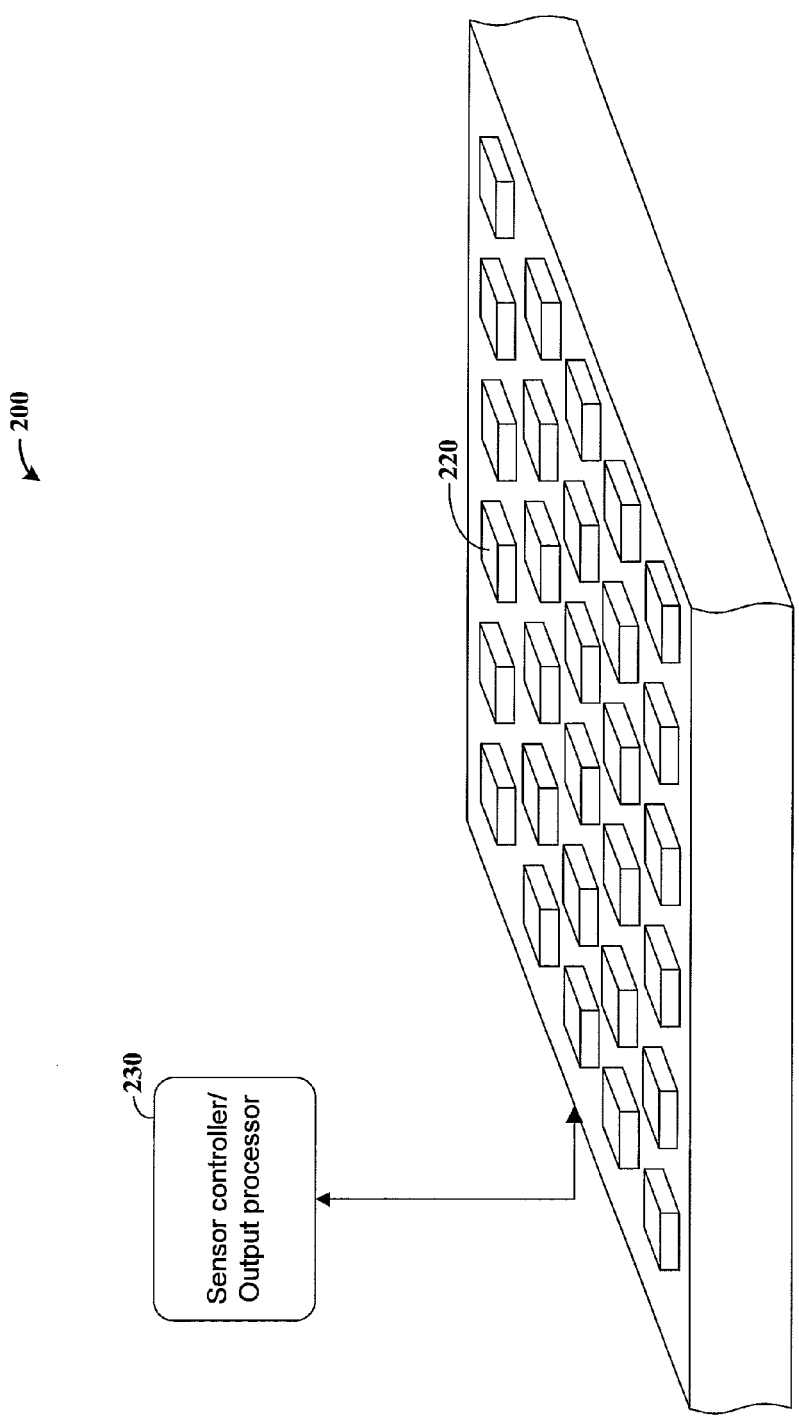
FIG. 2 shows an organic sensor arrangement that employs a plurality of different organic sensors, according to another example embodiment of the present invention.

FIG. 2 shows an organic sensor arrangement 200 that employs a plurality of different organic sensors, according to another example embodiment of the present invention. For discussion purposes, sensor 220 is labeled and the remaining sensors are shown arranged in an array pattern, and may be implemented using a sensor such as that shown in FIG. 1. However, for various embodiments, the sensor 220 is implemented as described with one or more of the shown sensors, in the shown arrangement and/or in other arrangements exhibiting fewer or more sensors and spatially arranged in a variety of manners.

Each sensor includes an OTFT, such as that described above, that is operable at low voltage to sense characteristics of an aqueous solution, such as analytes in the solution or other solution properties such as pH. Each of the sensors is coupled to a sensor controller/output processor 230 that operates each sensor by applying a voltage to a gate of the OTFT, and that is further coupled to detect an output (i.e., drain current) from each OTFT to characterize the solution.

At least some of the sensors in the arrangement 200 operate differently, relative to exposure to certain solutions and analytes therein. That is, sensors have different compositions, different arrangements or are treated to facilitate the detection of different solution characteristics. This differentiation among sensors is tailored to the particular application or otherwise, depending upon the implementation of the arrangement 200. For example, the sensors may be arranged with OTFTs having different physical arrangements or different compositions, such as different channel materials or different dielectric materials. The ability to control the film morphology provides yet another degree of versatility directly influencing the pathway for analyte molecules to the semiconductor-dielectric interface (with interaction as described above).

In other applications, sensors in the arrangement 200 are modified with receptor sites to facilitate interactions with specific analytes, or are modified to mitigate certain interactions (e.g., to repel certain molecules to facilitate the detection of other molecules). For example, certain sensors in the arrangement 200 are implemented with organic semiconductors having binding sites for selective chemical and biological detection. Referring back to FIG. 1, where the sensor device 100 is used in the arrangement 200 of FIG. 2, the channel 115 can be modified with receptor sites to facilitate or mitigate interaction.

In still other applications, one or more of the sensors in the arrangement 200 includes a semi-permeable membrane, or is otherwise arranged with such a membrane, that facilitates interaction between the sensor and selected analytes. For example, referring to sensor 220 as an example, such a membrane may be formed around or over the sensor and, as appropriate, other adjacent sensors in the arrangement 200.

One or more of the above-discussed approaches are implemented with the arrangement 200 to facilitate different operation of the individual sensors. With this approach, a few, tens or hundreds of different sensors can be implemented with a common arrangement and for different applications.

While shown as a single device, the sensor controller/output processor 230 is implemented with separate devices. In some applications, the sensor controller/output processor 230 includes different devices for respectively controlling the sensors and detecting an output from the sensors. In other applications, the sensor controller/output processor 230 is includes different devices for controlling and/or detecting an output from different sensors.

FIG. 3 shows flow cell sensor arrangement 300 for detecting chemicals in aqueous solutions, according to another example embodiment of the present invention. The flow cell arrangement 300 is fabricated on the surface of an OTFT including a PVP-HDA gate dielectric 310 having a thickness of about 22 nm, with a DDFTTF semiconductor material 320 at a thickness of about 40 nm. A top-contact structure with interdigitated source-drain electrodes (e.g., such as that shown in FIG. 1 with W=4 mm, L=50 μm) is used for electrode contact, here shown underneath a PDMS (polydimethylsiloxane) block 330. During manufacture and prior to removing a shadow mask defining the source-drain electrodes, the electrodes in the channel region are coated with a 50 nm layer of thermally evaporated silicon monoxide to reduce the influence of charge screening on the drain current. The PDMS block 330 is molded with a flow channel fed by an inlet 340 and passing solution via an outlet 350, and is laminated onto the OTFT source-drain channel region and secured with an aluminum substrate holder.

The flow cell sensor arrangement 300 and similar approaches can be implemented for detection with a multitude of solutions and, where appropriate, using different sensors as described in connection with FIG. 2 above. For example, various embodiments are directed to monitoring glucose and amino acids, to recognition of human exposure to toxic nerve agents such as Sarin or V-series agents by detecting for their metabolized product, methylphosphonic acid (MPA), or to detecting trinitrotoluene.

Consistent with the above discussion of embodiments, the following characterizes various example experimental embodiments.

Soluble oligothiophenes are deposited in the formation of OTFTs by drop-casting from a bromobenzene solution at 90° C. in a saturated bromobenzene vapor with a substrate temperature held at about 90° C. Top-contact OTFTs fabricated of highly crystalline thin films of trimethyl-[2,2';5',2''; 5'',2''']quaterthiophen-5-yl-silane (4TTMS) and 5,5'''-dicyclohexyl-[2,2';5',2'';5'',2''']quaterthiophene (CH4T) on PVP-HDA exhibit mobilities as high as 0.08 $cm^2$/Vs and 0.025 $cm^2$/Vs, respectively, and on/off ratios of greater than $2\times10^3$ at 1 V. Additional OTFT characteristics are available in the supporting discussion below.

Flexible OTFTs are formed on aluminum foil substrates, which also serve as the gate electrodes for the OTFTs. An 80 nm PVP-HDA layer is used as the insulating layer to compensate for the roughness of the underlying aluminum foil. After fabrication, the flexible device demonstrates nearly ideal transistor characteristics. A slight decrease in the source-drain current is obtained when the substrate is rolled around a 3.5 mm radius glass rod, with the channel direction oriented parallel to the bending direction. A further decrease in $I_{DS}$ is obtained at very low bending radii, such as 1 mm. In various implementations, $I_{DS}$ is partially recovered after removing the strain. The device performance is reasonably stable with a $\mu\sim$0.2-0.25 cm$^2$/Vs and an on/off ratio of $6\times10^3$-$1.1\times10^4$.

Studies of OTFT operation under aqueous conditions are performed in a static environment using top-contact OTFTs with PVP-HDA (22 nm) and DDFTTF (40 nm) films. A droplet of DI water is placed across the channel region and output and transfer characteristics are measured. Although the presence of water results in a slight increase in the source-drain current compared to the dry state, the transistor continues to function acceptably. Slight hysteresis is observed for the $I_{DS}$ versus $V_G$ curves. The thickness of the DDFTTF semiconductor layer is selectively reduced to as thin as 25 nm, retaining stable transistor operation and adequate performance.

Long-term operational stability of the OTFTs in an aqueous system is demonstrated by cycling the gate bias between 0.3 V and −1 V for over $10^4$ cycles while keeping a constant source-drain bias, $V_{DS}$=−0.6 V. No significant change in the transfer characteristics is observed. This approach is applicable to repeated analysis. In some applications, the source-drain bias is reduced to about −0.6 V to limit the influence of electrolytic hydrolysis and ionic conduction through the analyte solution on the measured drain current. OTFT operation under water is not limited to DDFTTF, but design restraint is selectively placed on the active layer material such that close packing is achieved with hydrophobic, aliphatic side groups. These materials are also very stable under ambient conditions that can be used for operation under aqueous conditions.

Electrical measurements are carried out at room temperature in air using a Keithley 4200SCS semiconductor parameter analyzer and a standard probe station setup. Voltage-dependant capacitance measurements are performed using an HP 4192 LF Impedance Analyzer for frequencies ranging between 10 Hz and 100 KHz.

When implemented, cross-linkable polymer gate dielectric films are selectively prepared according to the following method. Highly doped n$^{++}$ Si(100) substrates (R<0.008 ohm-cm) are cleaned by sonication in an industrial grade soap solution, rinsed with copious amounts of water, and blown dry with filtered (Mykrolis) nitrogen. Prior to spin-casting the dielectric layer, the substrates are treated with UV-Ozone (Jelight, Model 42) for 20 min. Aluminum foil (e.g., available from Reynolds) substrates are secured to a glass slide using Kapton® tape. These substrates are then rinsed with isopropanol and cleaned with O$_2$ plasma (Technic Micro-RIE Series 800) with 65 W power and 200 mTorr O$_2$. Solutions of poly(4-vinylphenol) (PVP) are prepared with a cross-linking agent in a molar ratio of 10:1 based on the PVP monomer in propylene glycol monomethyl ether acetate (PGMEA). The concentration of PVP is varied between 10-50 mg/mL. Crosslinkers investigated include 4,4'-(hexafluoroisopropylidene)diphthalic anhydride (HDA), which is mixed with a 3% triethylamine catalyst, and suberoyl chloride (SC). The solutions are filtered through a 0.2 μm syringe filter and spin-cast onto the cleaned substrates at a rate ranging between 3K-7K rpm for 1 minute using a (Headway Research, Inc.) spin-coater. The substrates are then cured on a hotplate at 90° C. for 2 hr to remove the solvent. The thickness of the dielectric layer is nominally controlled by the solution concentration and spin rate, and characterized using ellipsometry (Optrel GdBR Multiscope at a 70° angle of incidence under Nulling conditions with a 532 nm laser with a beam diameter and spot size of 0.6 mm and 20 mV, respectively) and atomic force microscopy (AFM) (Digital Instruments Nanoscope IV) operated in tapping mode (~300 kHz frequency, Si tip). A nearly linear correlation between concentration and thickness is obtained for solutions less than 50 mg/mL, which is expected for dilute polymer solutions. Sandwich electrode capacitance structures are constructed by depositing gold electrodes (0.9 mm$^2$, 0.2 mm$^2$, & 0.09 mm$^2$) on the surface of PVP-HDA and PVP-SC layers on highly doped silicon substrates.

The dielectric surface is selectively treated with octadecyltriethoxysilane (OTS). PVP-HDA substrates are placed in a glass dessicator with 50 μL OTS. Using a mechanical pump, the system is slowly evacuated to about 30 mTorr and heated to 100° C. in a sand bath for 48 hours. After the dessicator is cooled to room temperature and vented with air, the substrates are placed on a hotplate at 100° C. for 10 min, and then rinsed with toluene, acetone, and ethanol. An increase in thickness of 2 nm (e.g., determined by ellipsometry) is obtained following the OTS treatment.

OTFTs are selectively fabricated using high-vacuum and solution-processing techniques. Semiconductor thin-films are deposited by thermal evaporation (Angstrom Engineering, Inc.) at a rate of 0.3-0.5 Å/s under a pressure of $5.0\times10^{-7}$ Torr. The substrate temperature is controlled by heating a copper block during deposition. P-channel semiconductors, pentacene and 5,5'-bis-(7-dodecyl-9H-fluoren-2-yl)-2,2'-bithiophene (DDFTTF), are deposited at a substrate temperature ($T_{sub}$) of 65° C. and 90° C., respectively, to a thickness of 40 nm. The n-channel material FCuPc is similarly deposited at a $T_{sub}$ of 105° C. Films are deposited from solution using a drop-casting technique with a saturated solution in bromobenzene at 90° C. in a closed system. The top-contact devices are completed with gold electrodes thermally evaporated at a rate of 1 Å/s with a rotating substrate. Electrode dimensions are defined by a shadow mask with a W/L of 20, where L varied from 50-200 μm.

OTFT operation under aqueous conditions is effected in different manners. In one example, a droplet of de-ionized water is placed across an array of electrodes to which 20 nm gold wire probes are attached. Immediately after the addition of addition of the droplet, the characteristics are recorded. For OTFTs fabricated with 25 nm and 40 nm films of DDFTTF, the transistors functioned acceptably; for 10 nm DDFTTF film, a clear field-effect is observed.

OTFTs fabricated with pentance, FCuPc, CuPc, and CH4T, can be tested in static aqueous conditions. Immediately after the addition of water, the OTFTs with pentacene active layers show adequate semiconductor characteristics, which degrade. Surprisingly, a field-effect is obtained with the n-channel material, FCuPc, but with a very low on/off ratio of less than 2. Solution-processed OTFTs of 4TTMS and CH4T also function under aqueous conditions; however, long-term stability can be limited by a gradual delamination of the crystalline film while undergoing $V_G$ cycles [0.3 . . . −1 V].

A flow cell apparatus can be used to perform aqueous chemical detection. A poly(dimethylsiloxane) (PDMS)

block (3 cm×1 cm×8 mm) is molded with a flow channel of dimensions 2 cm×4 mm×500 μm and 1 mm diameter vertical inlet and outlet ports and laminated on the surface of a top-contact OTFT, with the transistor channel region aligned perpendicular to the flow direction in the flow channel. An aluminum substrate holder is used to secure the PDMS block to the OTFT substrate. The inlet flow is driven by a peristaltic pump (VWR variable flow pump) equipped with a manual flow switch for solution exchanges.

Materials used include materials as received from Aldrich and as otherwise stated. Pentacene is purified by temperature gradient sublimation in a three-zone furnace ($10^{-6}$ Torr, 220° C.). Copper(II) 1,2,3,4,8,9,10,11,15,16,17,18,22,23,24,25-hexadecafluoro-29H,31H-phthalocyanine (FCuPc) is washed with methanol and acetone. Poly-4-vinylphenol (PVP) as available from Aldrich has a $M_w$=20,000. Propylene glycol monomethyl ether acetate (PGMEA) is available from Alfa Aesar.

Nuclear magnetic resonance (NMR) spectra can be recorded on a Varian Mercury-400 MHz spectrometer. Chemical shifts (δ) are reported in parts per million, and the residual solvent peak can be used as an internal standard.

For Trimethyl-[2,2';5',2'';5'',2''']quaterthiophen-5-yl-silane (4TTMS) can be implemented as follows: 5-bromo-[2,2']bithiophene (0.49 g, 1.99 mmol) and trimethyl-(5'-tributylstannanyl-[2,2']bithiophenyl-5-yl)-silane (1.0 g, 1.90 mmol) in 20 mL of anhydrous dimethylformamide are added to a nitrogen flushed 2-neck flask. The solution is degassed using freeze-pump-thaw until no gas evolved. [1,1'-Bis (diphenylphosphino)ferrocene]dichloropalladium(II) (77 mg, 0.095 mmol) is added and the reaction mixture is heated to 90° C. for 24 hrs. After cooling to room temperature, the mixture is poured into methanol and the precipitate is filtered. The crude product is flashed through silica gel in chloroform (566 mg, 74%). The product is further purified by temperature gradient sublimation at 10-6 Torr and collected at ca. 160° C.). $^1$H NMR (CDCl$_3$, 400 MHz): $\delta_H$ 7.23 (d, J=3.6 Hz, 2H), 7.18 (d, J=4.0 Hz, 1H), 7.14 (d, J=3.6 Hz, 1H), 7.07-7.10 (m, 4H), 7.03 (dd, J=4.8, J=4.8 Hz, 1H), 0.33 (s, 9H). MS (DEI) m/z: 403 (M+)

For Trimethyl-(5'-tributylstannanyl-[2,2']bithiophenyl-5-yl)-silane, [2,2']bithiophene (10.34 g, 62.19 mmol) in 100 mL anhydrous tetrahydrofuran is added to a nitrogen flushed 3-neck flask. The solution is bubbled with nitrogen for 30 min, then cooled to −78° C. Then, n-BuLi (12.69 g, 62.65 mmol) is added drop-wise over 30 min and the mixture is stirred for 1.5 hr, then brought 25° C. After stirring for 30 min, chlorotrimethylsilane (6.76 g, 62.19 mmol) is added portion-wise and the mixture is stirred for 2 hr. The reaction mixture is again cooled to −78° C. and n-BuLi (12.69 g, 62.65 mmol) is added drop-wise over 15 min. The mixture is stirred for 1 hr, and then allowed to warm to 25° C. for 1 hr followed by quenching with tributyltin chloride (20.39 g, 62.65 mmol). The mixture is allowed to stir overnight, and then poured into 250 mL hexanes. The solution is washed with 125 mL 5% NH$_4$Cl (×3) and H$_2$O (×3). The solution is dried over MgSO$_4$, then the solvent is removed by evaporation at reduced pressure. $^1$H NMR (CDCl$_3$, 400 MHz): $\delta_H$ 7.32 (dd, J=3.2 Hz, J=2.4 Hz, 1H), 7.25 (dd, J=3.2 Hz, J=3.2 Hz, 1H), 7.14 (dd, J=3.2 Hz, J=1.6 Hz, 1H), 7.08 (dd, J=3.2 Hz, J=2.0 Hz, 1H), 1.56-1.64 (pent., J=7.6 Hz, 6H), 1.32-1.41 (sext., J=7.2 Hz, 6H), 7.12-7.16 (t, J=7.6 Hz, 6H), 0.91-0.94 (t, J=7.6 Hz, 9H), 0.34 (s, 9H).

The influence of pH on OTFT performance (as a pH sensor) can be characterized through a series of control experiments. pH solutions are made from stock 1 M solution of HCl and NaOH. For solutions of pH<7, the ions present are hydronium (H$_3$O$^+$), chlorine (Cl$^-$) and hydroxide (OH$^-$). For solutions with a pH of >7, the ions present are hydronium (H$_3$O$^+$), sodium (Na$^+$) and hydroxide (OH$^-$).

In a first control experiment, the drain current response is obtained to a solution of 0.001 M NaCl with equivalent NaCl concentration in pH 3 or pH 11 solution. There is a slight increase, and then a decrease in drain current. Based on the magnitude of current change, the OTFT drain current responds generally depending upon either the hydronium or hydroxide ions (e.g., not resulting from either sodium or chlorine atoms). The OTFT exhibits an increase in current when water is flowed over the channel region. When all of the water is not instantaneously removed for the substrates, the decrease in current as water is removed is gradual and constant after an initial shift. Since the drain current initially increases on exposure of the device to water and increases further with hydronium ion concentration (pH), current shift is related to a local change in hydronium ion concentration.

While the present invention has been described above and in the claims that follow, those skilled in the art will recognize that many changes may be made thereto without departing from the spirit and scope of the present invention. Such changes may include, for example, interchanging materials, such as using other esters or urethanes as cross-linking materials in forming sensor dielectric layers, or using PVP-type materials other than those discussed in the dielectric layers. In addition, the thin films and approaches described herein are selectively implemented with one or more of a variety of devices and/or systems, such as capacitors, thin-film and other transistors, optical devices, other semiconductor applications and devices or systems implemented for one or both if organic and inorganic applications involving sensors and other devices. Other applications are directed to those characterized in the above-referenced provisional patent application (and the appendices that form a portion of the provisional patent application) to which benefit is claimed and which is further incorporated herein by reference. Moreover, one or more of the approaches and/or devices herein are implemented for use with applications such as those described and/or referenced in Yoon, M-H; Yan, H.; Facchetti, A; and Marks, T. J. *Low-Voltage Organic Field-Effect Transistors and Inverters Enabled by Ultrathin Cross-Linked Polymers as Gate Dielectrics*, J. Am. Chem. Soc., 2005, 127, 10388-10395, which is fully incorporated herein by reference. These and other approaches as described in the contemplated claims below characterize aspects of the present invention.

What is claimed is:

1. A method comprising:
   providing an organic transistor including a gate and including a source, a drain, and an organic semiconducting channel therebetween and with exposed portions of each of the source, drain and channel for permitting direct interaction between each of the source, drain and channel with an aqueous solution;
   presenting the aqueous solution to the exposed portions;
   presenting a low voltage to the gate; and
   sensing, in response to the steps of presenting and to direct chemical interaction between the aqueous solution and the channel while the aqueous solution is also in direct contact with both the source and drain, characteristics of the aqueous solution based on the direct chemical interaction between the aqueous solution and the channel.

2. The method of claim 1, wherein
   sensing characteristics of the aqueous solution includes sensing a change in current flowing between the source and drain via the channel as altered by interaction between a material in the solution and the channel, and sensing a type of the material based on the change in current, and presenting the low voltage to the gate includes presenting a voltage of less than about 2 V to the gate that biases the channel to provide the current flow between the source and drain for the sensing of the change in current flowing, and that is sufficiently low to provide about no electrolytic hydrolysis or ionic conduction between the source and drain and through the material in the solution while the change in current is detected.

3. The method of claim 1, wherein providing the organic transistor includes providing a dielectric layer between the gate and the channel, and wherein presenting the low voltage to the gate includes presenting a voltage that is less than about 2 V to the gate and using the voltage and the dielectric layer to apply an electric field to the channel that switches the channel to a conducting state via which the source and drain are electrically coupled.

4. The method of claim 3, wherein presenting the low voltage to the gate includes presenting a voltage that is about 1 V and using the 1 V with the dielectric layer to switch the channel to the conducting state.

5. The method of claim 1, wherein providing the organic transistor includes providing a dielectric layer between the channel and the gate, and providing the channel with grain boundaries that facilitate the diffusion of small molecules or ions from the solution to an interface between the channel and the dielectric layer, presenting the aqueous solution to the exposed portions includes influencing charge transport in the channel by interacting the small molecules or ions with the channel while the low voltage is presented to the gate, thereby changing an amount of current that is passed in the channel between the source and drain.

6. An apparatus comprising:

an organic transistor including a gate and including a source, a drain, and an organic semiconducting channel therebetween and with exposed portions of each of the source, drain and channel, the source, drain and channel configured and arranged to directly interact with an aqueous solution;

means for presenting the aqueous solution in direct contact with the exposed portions of each of the channel, source and drain;

means for presenting a low voltage to the gate; and means for sensing, in response to the steps of presenting and to direct chemical interaction between the aqueous solution and the channel while the aqueous solution is also in direct contact with both the source and drain, characteristics of the aqueous solution based on the direct chemical interaction between the aqueous solution and the channel.

7. The apparatus of claim 6, wherein the means for sensing is configured and arranged to sense characteristics of the aqueous solution by sensing a change in current flowing between the source and drain via the channel as altered by interaction between a material in the solution and the channel, and sensing a type of the material is based on the change in current, and the means for presenting the low voltage to the gate is configured and arranged to present a voltage of less than about 2 V to the gate to bias the channel and to provide the current flow between the source and drain for the sensing of the change in current flowing, the voltage being sufficiently low to provide about no electrolytic hydrolysis or ionic conduction between the source and drain and through the material in the solution while the change in current is detected.

8. The apparatus of claim 6, wherein the organic transistor includes a dielectric layer between the gate and the channel, and wherein the means for presenting the low voltage to the gate is configured and arranged to present a voltage that is less than about 2 V to the gate and use the voltage and the dielectric layer to apply an electric field to the channel that switches the channel to a conducting state via which the source and drain are electrically coupled.

9. The apparatus of claim 8, wherein the means for presenting the low voltage to the gate is configured and arranged to present a voltage that is about 1 V to the gate and use the 1 V with the dielectric layer to switch the channel to the conducting state.

10. The apparatus of claim 6, wherein the organic transistor includes a dielectric layer between the channel and the gate;

the channel has grain boundaries that facilitate the diffusion of small molecules or ions from the solution to an interface between the channel and the dielectric layer; and the means for presenting the aqueous solution to the exposed portions is configured and arranged to influence charge transport in the channel by interacting the small molecules or ions with the channel while the low voltage is presented to the gate, thereby changing an amount of current that is passed in the channel between the source and drain.

11. An apparatus comprising:

an organic semiconducting channel having a conductivity characteristic and being configured and arranged to chemically interact with material in an aqueous solution in contact with the organic semiconducting channel, and to effect a change in the conductivity characteristic via the chemical interaction;

a gate configured and arranged to apply a bias to the organic semiconducting channel;

a dielectric layer electrically arranged between the gate and the organic semiconducting channel; and source and drain electrodes connected to opposing ends of the organic semiconducting channel, the source and drain electrodes being configured and arranged as an organic transistor with the channel, the gate and the dielectric layer to characterize the material in the solution by responding to a low voltage at the gate by conducting current through the channel while the source and drain electrodes are in direct contact with the aqueous solution, and providing a characterization of the material in the aqueous solution by altering the flow of the current through the channel, via the chemical interaction of the organic semiconductor with the material in the aqueous solution, while the aqueous solution is in direct contact with the source and the drain.

12. The apparatus of claim 11, wherein the channel, gate and dielectric layer are configured and arranged to facilitate switching of the channel to electrically couple the source and drain in response to a low voltage that is less than about 2 V applied to the gate, by providing a detectable change in the current through the channel via the chemical interaction at the low voltage while providing about no electrolytic hydrolysis or ionic conduction between the source and drain through the material in the solution.

13. The apparatus of claim 11, wherein the source, drain, gate and dielectric layer are configured and arranged with the organic semiconducting channel to, using a voltage that is less than about 2 V being applied to the gate, apply an electric field to the channel that switches the channel to a conducting state, and manifest a change in current flow through the organic semiconducting channel that is based on the chemical interaction while providing about no electrolytic hydrolysis or ionic conduction between the source and drain through the material in the solution.

14. The apparatus of claim 11, wherein the channel has grain boundaries that facilitate the diffusion of small molecules or ions from the solution to an interface between the channel and the dielectric layer, and wherein the source, drain, gate and dielectric layer are configured and arranged with the organic semiconducting channel to provide the characterization of the material based on changes in the current flow due to the diffusion of the small molecules or ions into the channel while the low voltage is applied to the gate and under conditions in which about no current flows between the source and drain via the solution.

15. The apparatus of claim 11, wherein the channel, gate electrode and dielectric layer are configured and arranged to facilitate a detectable change in the current flow between the source and drain region through the channel while the dielectric layer is exposed to the aqueous solution.

16. The apparatus of claim 11, wherein the organic semiconducting channel includes one of: carbon nanotube, a carbon nanotube film, and a polymer.

17. The apparatus of claim 11, further including a semipermeable membrane configured and arranged to control the contact of the aqueous solution to the channel.

18. The apparatus of claim 11, further including
a first material coupled to the channel and being selective to an analyte, the first material and channel being configured and arranged to facilitate coupling of the analyte from the solution to the channel for providing a characterization of the analyte, and
a second material coupled to the channel and configured and arranged with the channel to deter a selected substance in the aqueous solution, thereby mitigating any effect of the selected substance upon the current flow through the channel.

19. An apparatus comprising:
a plurality of organic thin film transistors (OTFTs), each OTFT having a gate, source, drain, an organic semiconducting channel between the source and drain, and a dielectric layer between the gate and channel, the channel being configured and arranged to chemically interact with an analyte in an aqueous solution and to effect, via the chemical interaction, a change in an amount of current passing between the source and drain through the channel, while a low voltage is applied to the gate and while the source, drain and channel are in direct contact with the solution;
a fluid channel configured and arranged to place the aqueous solution in direct contact with the source, drain and channel of each OTFT while the voltage is applied to the gate;
a controller configured and arranged to apply the low voltage to the gate of each of the OTFTs; and
a detector electrically coupled to the source and drain of each of the OTFTs and configured and arranged to detect a characteristic of the aqueous solution to which the channel of each OTFT is exposed based upon a change in current passing between the source and drain through the channel, while the source, drain and channel are in direct contact with the solution.

20. The apparatus of claim 19, wherein the channel, gate and dielectric layer are configured and arranged to facilitate switching of the channel to electrically couple the source and drain in response to a low voltage that is less than about 2 V applied to the gate, by providing a detectable change in the current passing through the channel via the chemical interaction at the low voltage, while providing about no electrolytic hydrolysis or ionic conduction between the source and drain through the analyte in the solution.

21. The apparatus of claim 19, wherein different ones of the channels have different organic materials that are configured and arranged to exhibit different electrical responses to interaction with different types of materials in the aqueous solution, thereby providing different characterizations of the different types of materials based on different changes in the amount of current passing in each respective channel.

* * * * *